United States Patent [19]

Okano et al.

[11] Patent Number: 5,716,317
[45] Date of Patent: Feb. 10, 1998

[54] SHEATH FOR SYRINGE BARREL

[75] Inventors: Sakae Okano, Sodegaura; Yoshimasa Tanaka, Sanda; Hisao Tobiki, Tokyo, all of Japan

[73] Assignee: Nihon Medi-Physics Co., Ltd., Nishinomiya, Japan

[21] Appl. No.: 352,738

[22] Filed: Dec. 2, 1994

[30] Foreign Application Priority Data

Dec. 6, 1993 [JP] Japan .................. 5-339709

[51] Int. Cl.⁶ .................................................. A61B 6/00
[52] U.S. Cl. ....................................................... 600/4; 600/5
[58] Field of Search .................. 600/3, 4, 5; 604/197, 604/199, 192

[56] References Cited

U.S. PATENT DOCUMENTS

| | | | |
|---|---|---|---|
| 1,830,453 | 11/1931 | Wassmer | 600/4 |
| 3,673,411 | 6/1972 | Glasser | 600/5 X |
| 3,820,541 | 6/1974 | Langan | 600/5 X |
| 4,048,997 | 9/1977 | Raghavachari et al. | 128/215 |
| 4,056,096 | 11/1977 | Collica et al. | 600/5 |
| 4,060,073 | 11/1977 | Collica et al. | 128/1.1 |
| 4,062,353 | 12/1977 | Foster | 600/5 |
| 4,122,836 | 10/1978 | Burnett | 600/5 |
| 4,364,376 | 12/1982 | Bigham | 600/5 |
| 4,393,864 | 7/1983 | Galkin et al. | 600/5 |
| 4,401,108 | 8/1983 | Galkin et al. | 600/5 |
| 4,615,468 | 10/1986 | Gay | 222/327 |
| 4,638,909 | 1/1987 | Kuperus | 600/4 |
| 4,994,012 | 2/1991 | Nakayama et al. | 600/5 |
| 5,053,019 | 10/1991 | Duffy | 600/4 X |

FOREIGN PATENT DOCUMENTS

| | | |
|---|---|---|
| 0550767A1 | 7/1993 | European Pat. Off. . |
| 2-12997 | 4/1990 | Japan . |

OTHER PUBLICATIONS

Patent Abstracts of Japan, vol. 015, No. 189 (C–0831), 15 May 1991, JP–A–03 047 273, Daiichi Rajio Isotope Kenkyusho:KK, 28 Feb. 1991, Three–Way Cock.

*Primary Examiner*—Sam Rimell
*Attorney, Agent, or Firm*—Jones, Tullar & Cooper, P.C.

[57] ABSTRACT

A sheath for a syringe barrel, includes a main body in which a radiation shielding device for holding a syringe filled with pharmaceutical liquid therein is fitted, a male luer provided at a front end of the main body and designed to set a disposable needle, and a transfixing needle extending backward from inside of the male luer to penetrate a rubber plug at an opening at a front end of a syringe held in the main body.

17 Claims, 14 Drawing Sheets

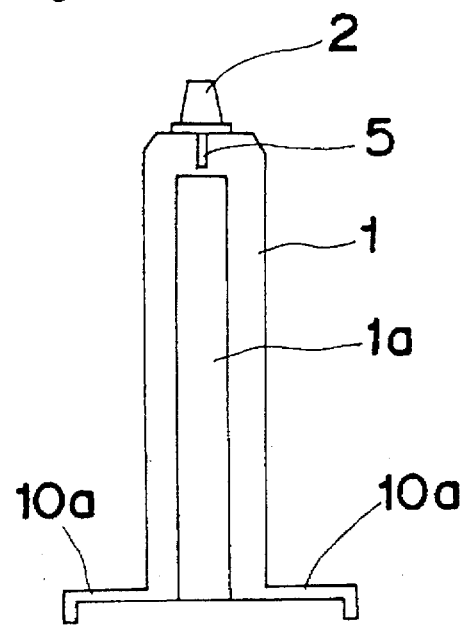
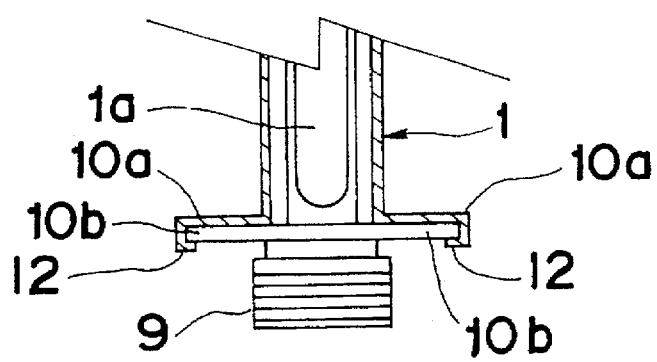
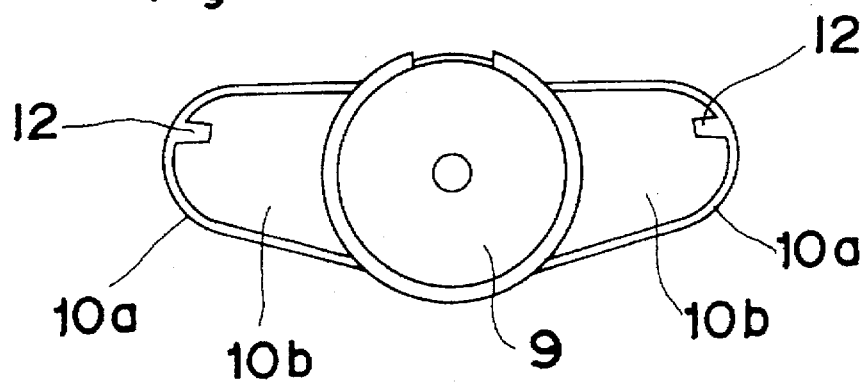

SHEATH FOR SYRINGE BARREL

BACKGROUND OF THE INVENTION

The present invention relates to a syringe for medical use, and more particularly to a sheath for a syringe barrel having pharmaceutical liquid preliminarily filled therein to which a disposable needle is adapted to set.

In an example of a conventionally-used syringe, as shown in FIG. 21, while pharmaceutical liquid is filled in a main body 13 of a syringe barrel, an opening of the front end of the main body 13 is sealed by a rubber plug 14, with a rear end thereof shut by a gasket 15. When the syringe of the above type, namely, having pharmaceutical liquid preliminarily filled therein is to be used, a plunger 16 is attached to the gasket 15 of the syringe and further a syringe luer tip 17 and a double-sided needle 18 are mounted.

Since changing of radioactive pharmaceutical liquid is not required in the above syringe, the syringe has been widely used particularly in the field handling radioactive drugs so that a working operator is less exposed to radioactive rays. In injecting radioactive pharmaceutical liquid, a radiation shielding device 7 which has a see-through window 8 of lead glass at the side wall thereof as shown in FIGS. 22 and 23 is also used to accommodate the syringe.

In this case, however, drawbacks remain unsolved, namely: (1) whether a blood vessel is secured cannot be confirmed until the blood enters the syringe inside the radiation shielding device, and (2) a special double-sided needle is needed and a general-purpose disposable needle or a three-way cock or the like cannot be used, etc.

Meanwhile, a double luer needle-type syringe shown in FIG. 24 (Japanese Utility Model Laid-Open Publication No. 1-135949 (135949/1989) or a double-sided needle of FIG. 25 are proposed in order to solve the aforementioned drawbacks.

The double luer needle-type syringe of FIG. 24 is equipped with a syringe luer 17, a double-luer needle holder 19, and a disposable needle 21 when in use, and therefore, it is considerably difficult to inject pharmaceutical liquid through the double luer needle-type syringe due to an increased length of the needle part. Moreover, an operator may inadvertently hurt his or her fingers or hands by a transfixing needle 4' when preparing the syringe or disposing of the needle after use.

On the other hand, referring to the double-sided needle in FIG. 25, since a needle adapter 20 sets to cover up to the side face of the syringe, it becomes necessary to set the adapter 20 to the syringe before the syringe with the pharmaceutical liquid is accommodated in the radiation shielding device, thereby endangering the operator to radiation exposure. As the syringe barrel is increased in diameter by the thickness of the adapter, the radiation shielding device accommodating the barrel is consequently increased in diameter, eventually resulting in a bulky structure of the device with even the same shielding efficiency (the same thickness of the wall of the device). The device is inconvenient to handle.

Lately, the syringe containing the pharmaceutical liquid is sometimes transported from a pharmaceutical maker to a user while it is kept in the radiation shielding device. Therefore, in this state of transportation, the arrangement of FIG. 25 is disadvantageous in that the syringe filled with the pharmaceutical liquid must be taken outside the device to use it.

In addition, since it is necessary to hold and set an inclined cut-opening of the point of the needle up in any of the syringes noted above at the dosage of pharmaceutical liquid, the operator, and specifically the fingers or hands of the operator are exposed to radioactive rays leaking from the syringe.

SUMMARY OF THE INVENTION

Accordingly, an object of the present invention is to provide a sheath for a syringe barrel which allows the use of general-purpose disposable needles and effectively prevents an operator's fingers or hands from being hurt, and enables registering of a needle point before radioactive pharmaceutical liquid is set, thereby reducing the exposure of the fingers or hands of the operator to radioactive rays.

In accomplishing this and other objects, according to one aspect of the present invention, there is provided a sheath for a syringe barrel, comprising:

a main body in which a radiation shielding device for holding a syringe filled with pharmaceutical liquid therein is fitted;

a male luer provided at a front end of the main body and designed to set a disposable needle; and a transfixing needle extending backward from inside of the male luer to penetrate a rubber plug at an opening at a front end of a syringe held in the main body.

BRIEF DESCRIPTION OF THE DRAWINGS

These and other objects and features of the present invention will become clear from the following description taken in conjunction with the preferred embodiments thereof with reference to the accompanying drawings, in which:

FIG. 8 is a plan view of a syringe barrel sheath with flanges according to another embodiment of the present invention;

FIGS. 9 and 10 are a sectional plan view of a part of a syringe barrel sheath with flanges having hooks, according to a further embodiment of the present invention, and a bottom view of the syringe of FIG. 9 in FIG. 10;

DETAILED DESCRIPTION OF THE EMBODIMENTS

Figure 2:
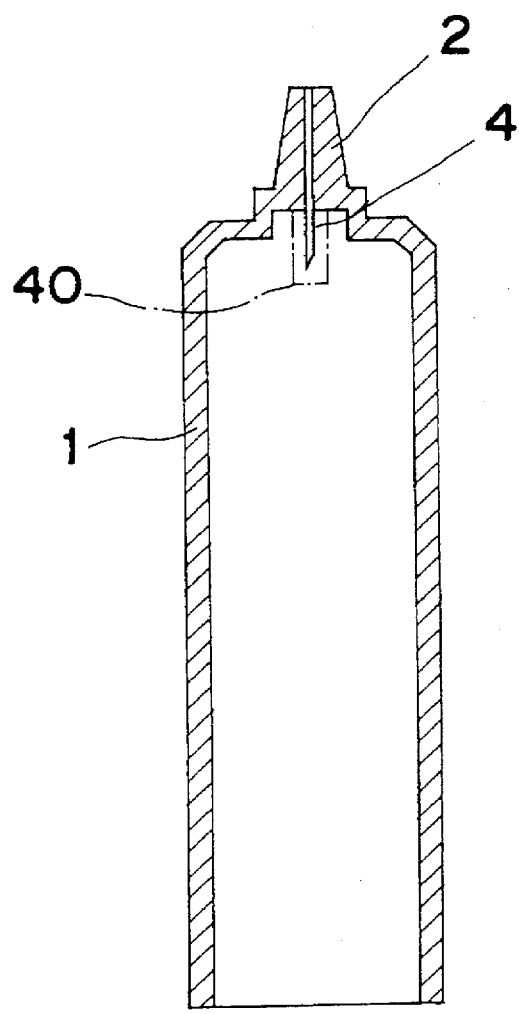
FIGS. 1 and 2 are a plan view and a sectional plan view of a syringe barrel sheath according to a first embodiment of the present invention.

Before the description of the present invention proceeds, it is to be noted that like parts are designated by like reference numerals throughout the accompanying drawings.

Preferred embodiments of the present invention will be depicted hereinbelow. The embodiments are merely descriptive examples of the present invention, not limiting the scope of the present invention.

At the same time, and for convenience sake, in each embodiment, a needle is supposed to be at the front side of a syringe barrel sheath (and the opposite is the rear side of the sheath) and a lead glass see-through window is at the upper side (and the opposite is the lower side) of the sheath in the description below.

Figure 1:
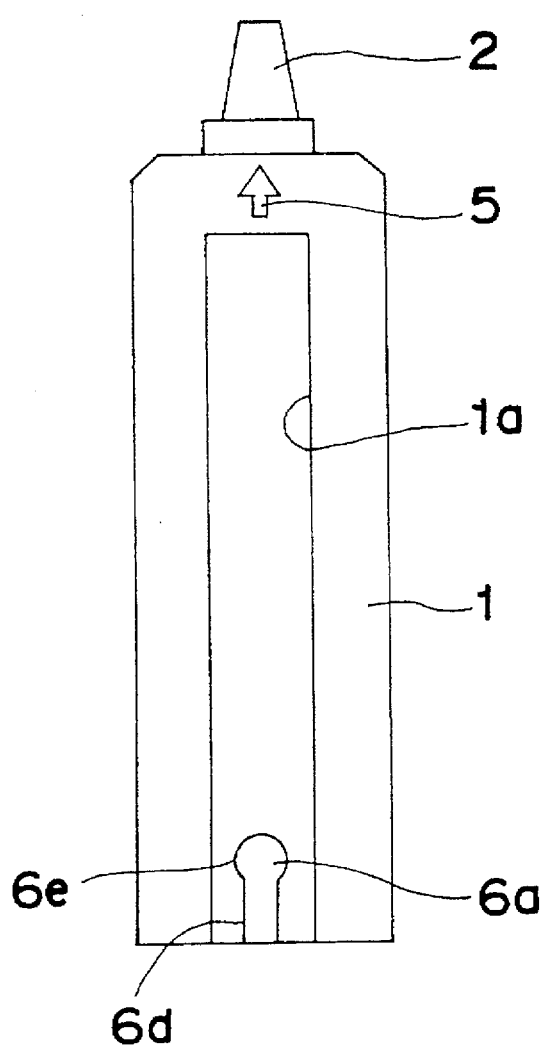
Figure 3:
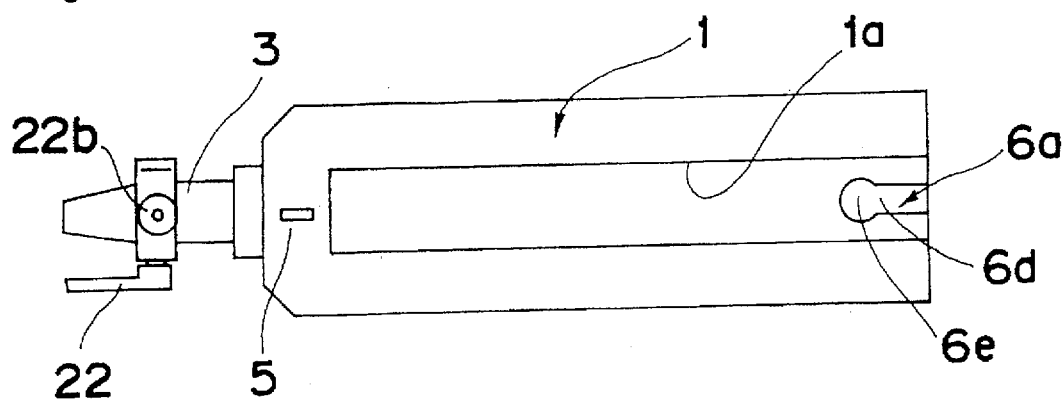
FIG. 3 is a plan view of a syringe barrel sheath with a three-way cock according to a second embodiment of the present invention.
Figure 4:
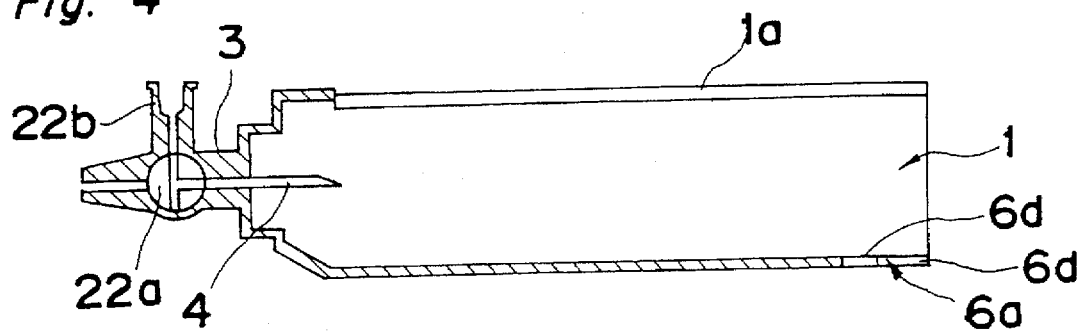
FIGS. 4, 5, and 6 are sectional views of the syringe barrel sheath shown in FIG. 3 with the three-way cock is changed in different directions.
Figure 5:
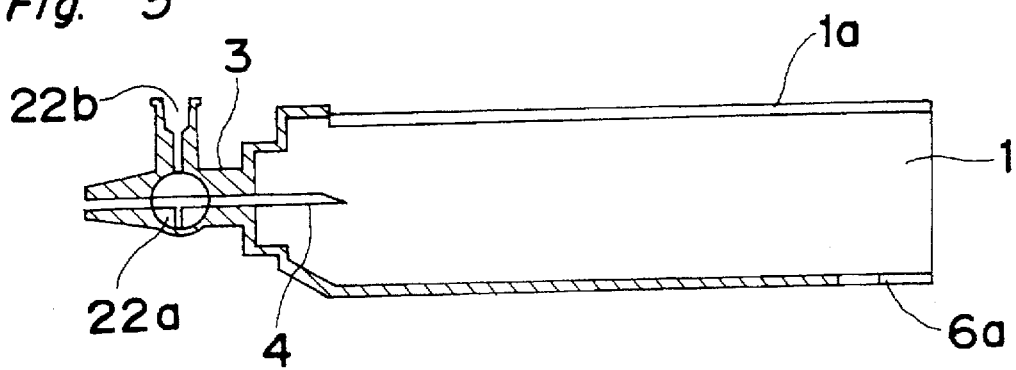
Figure 6:
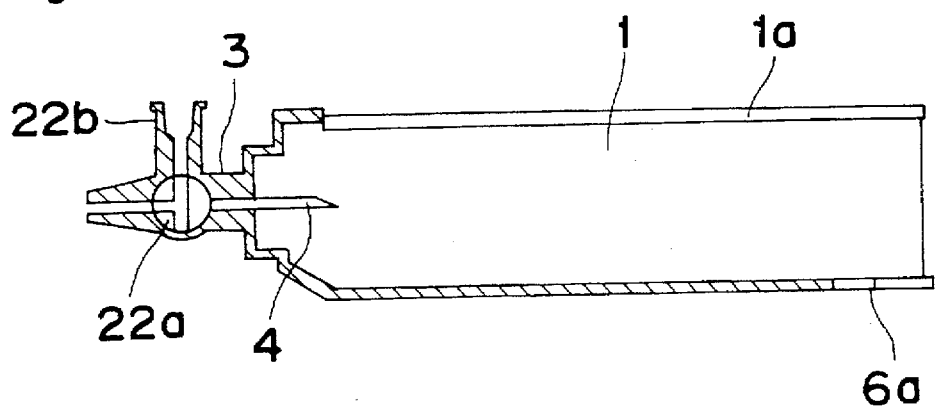
Figure 7:
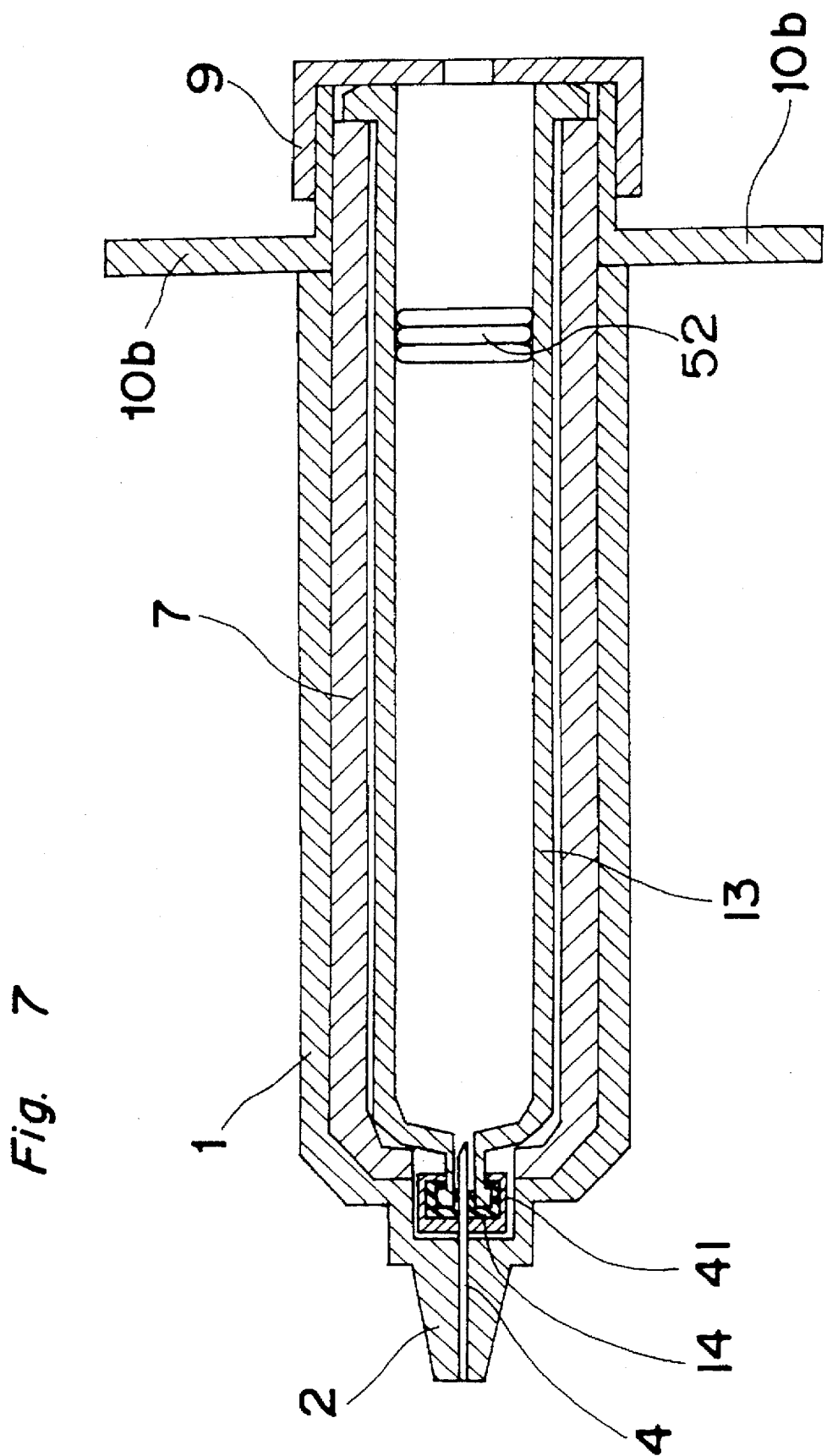
FIG. 7 is a sectional view of the syringe barrel sheath of FIG. 1 wherein a radiation shielding device is inserted.
Figure 26:
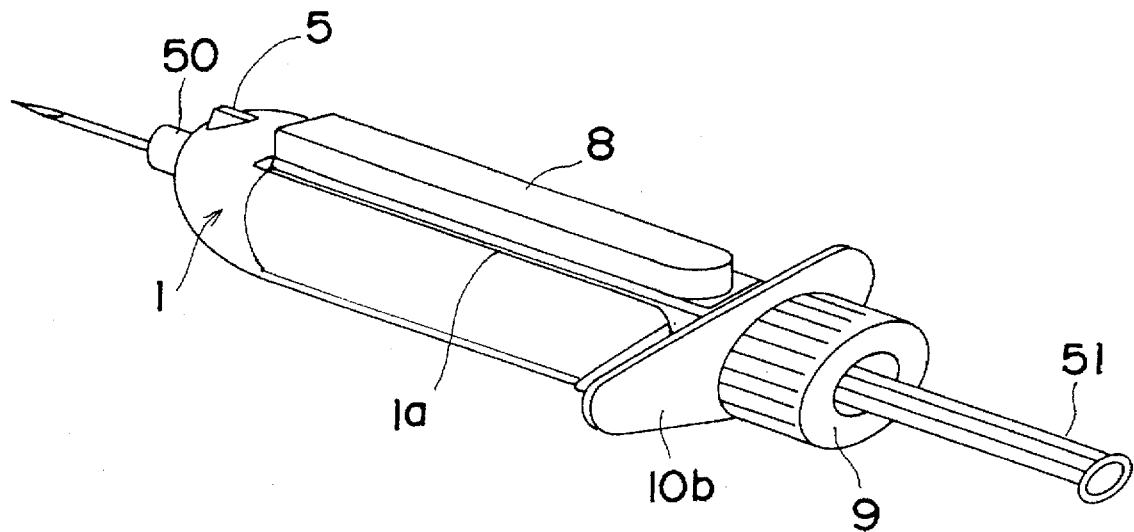
FIGS. 26 and 27 are a perspective view and a perspective view and a sectional view of a syringe barrel sheath according to a further embodiment of the present invention.
Figure 27:
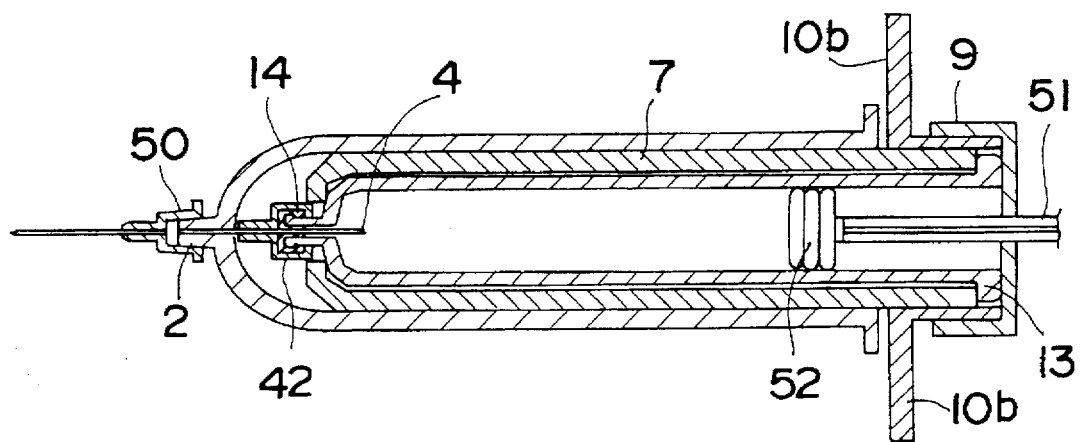

A barrel sheath according to a first embodiment of the present invention is constructed in a manner as indicated in FIGS. 1 and 2. More specifically, the sheath includes a main body 1 covering the radiation shielding device 7 with the see-through window 8 of lead glass at the side wall thereof, and a male luer 2 designed to mount a general-purpose disposable needle 50 at the front end of the main body 1 as shown in FIGS. 26 and 27. Further, the barrel sheath has a transfixing needle 4. The transfixing needle 4 is elongated from the front end of the male luer 2 toward the rear of the sheath through the inside of the male luer 2 to penetrate a rubber plug 14 at an opening at the front end of the syringe filled with pharmaceutical liquid and accommodated in the radiation shielding device 7. The rubber plug 14 is fixed at the opening at the front end of the syringe by a cap 41 as shown in FIG. 7.

A barrel sheath according to a second embodiment of the present invention is constructed in a manner as indicated in FIGS. 3 through 6. More specifically, the sheath includes the main body 1 covering the radiation shielding device 7, a male luer 3 having a three-way cock 22, and the transfixing needle 4. The cock 22 is used when bolus injection is performed. A syringe with a physiological salt solution is connected to a female luer 22b of the cock 22 via a tube and a tube of which a needle with flanges is fixed to an end instead of a disposable needle is attached to the male luer 3. The cock 22 is turned from a state shown in FIG. 4 to a state in FIG. 6 to fill the tubes with the physiological salt solution and then the needle with the flanges is inserted into the blood vessel of a patient. Thereafter, the plunger of the syringe with the physiological salt solution is pulled slightly to flow back blood in the tube to confirm that the needle is inserted into the blood vessel of the patient. The cock 22 is turned from the state shown in FIG. 6 to the state shown in FIG. 5 to inject the pharmaceutical liquid in the syringe held in the sheath to the patient and then cock 22 is turned from the state shown in FIG. 5 to the state shown in FIG. 6 to inject the physiological salt solution to the patient.

It is suitable that each barrel sheath is made of material light in weight and easy to sterilize, for example, plastic such as polycarbonate; polystyrene; more preferably, polypropylene, and polyethylene; or the like. Needless to say, transparent or colored material may be employed from the viewpoint of good appearance.

In FIGS. 1–7, the main body 1 extends immediately in front of flanges 10b of the radiation shielding device 7, with a cutaway 1a provided at a part corresponding to the lead glass see-through window 8 of the radiation shielding device 7. Therefore, when the radiation shielding device 7 is fitted into the main body 1 to cover the radiation shielding device 7 with the main body 1, the lead glass see-through window 8 of the radiation shielding device 7 is fitted into the cutaway 1a. A registering mark 5 is indicated in front of the lead glass see-through window 8. The registering mark 5 is used when the disposable needle 50 is fitted onto the male luer 2 or 3 so that an inclined cut-opening of the point of the disposable needle 50 is directed upwardly while the see-through window 8 is also directed upwardly. Moreover, a fixing notch 6a is formed at a position corresponding to a projection 11a of the radiation shielding device 7 shown in FIGS. 14 and 15. Therefore, when the radiation shielding device 7 is covered with the main body 1 and the lead glass see-through window 8 of the radiation shielding device 7 is fitted into the cutaway 1a, the projection 11a of the radiation shielding device 7 is fitted into the fixing notch 6a. The fixing notch 6a has a narrow cutaway 6d extended from the rear end of the main body 1 which has a width equal to or slightly less than the width of the projection 11a; and a fixing hole 6e located adjacent to the cutaway 6d in which the projection 11a is fitted. Thus, after the projection 11a is fitted in the hole 6e, it is not easy to remove the projection 11a from the hole 6e because of the presence of the cutaway 6d.

Each transfixing needle 4 of the first and second embodiments extends backward from inside of the male luer 2 or 3 of the main body 1. The length of the transfixing needle 4 makes it possible to pierce the rubber plug 14 at the opening at the front end of the syringe containing pharmaceutical liquid and set in the radiation shielding device 7. The transfixing needle 4 may not only be formed in one integral body with the main body 1 of the sheath by way of bonding or the like manner, but may be provided with a screw-type or lock-type detaching mechanism.

For using the sheath of each embodiment, as shown in FIGS. 26 and 27, the point of the disposable needle 50 is registered and mounted to the male luer 2 or 3 of the sheath. At the same time, the syringe containing the pharmaceutical liquid is accommodated in the radiation shielding device 7 (alternatively, the radiation shielding device 7 already storing the syringe therein is purchased), and a plunger 51 is set to a gasket 52 within the syringe. Then, the radiation shielding device 7 is inserted and fixed in the sheath for use.

Moreover, if the transfixing needle 4 is covered with a soft rubber protecting member 40 shown by a chain-dotted line in FIG. 2, an operator's fingers and hands can be protected by the member. When the transfixing needle is covered with the rubber protecting member 40 or the like, the barrel sheath equipped with the disposable needle is set to a subject person to thereby secure the blood vessel before the injection of pharmaceutical liquid. Thereafter, the radiation shielding device 7 having the syringe filled with the pharmaceutical liquid and the plunger 51 set therein is inserted into the sheath. In this way, the degree of exposure to radiation is further lessened. In this case, when the transfixing needle 4, penetrating the rubber protecting member 40, passes through the rubber plug 14 of the syringe, the rubber protecting member 40 is prevented from entering the syringe owing to the rubber plug 14, so that the transfixing needle 4 alone is allowed to enter the syringe.

The configuration of the main body 1 can be changed in a desired manner. For example, as shown in FIGS. 26 and 27, a cap 42 for fitting the rubber plug 14 at the opening at the front end of the syringe has a projected tubular portion at the front end thereof so that a gap is formed between the front end part of the radiation shielding device 7 covering the syringe and the inside of the main body 1, resulting in a round outer configuration of the main body 1.

Figure 11:
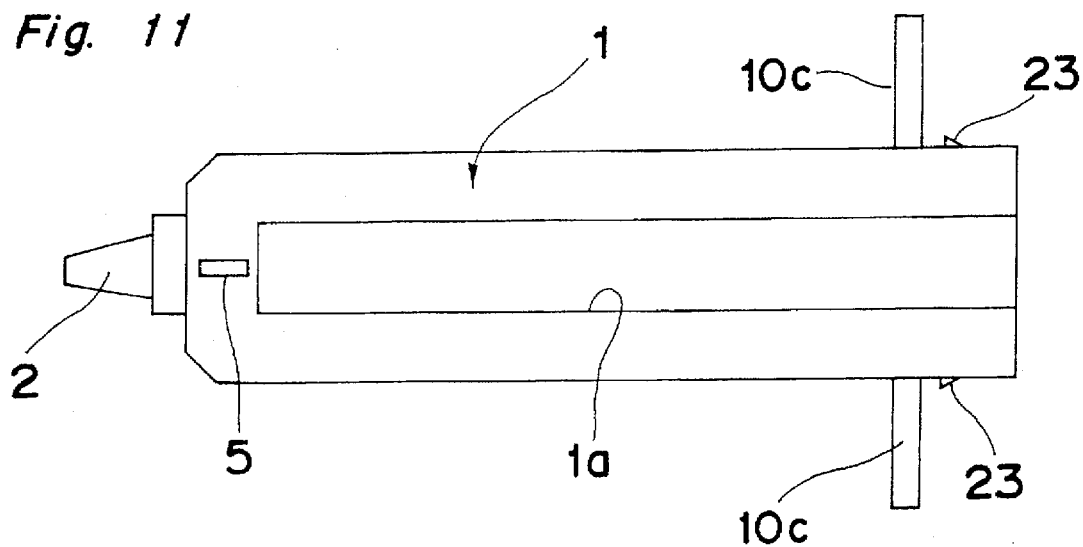
FIG. 11 is a plan view of a syringe barrel sheath with flanges only at the side of the sheath according to a still further embodiment of the present invention.
Figure 12:
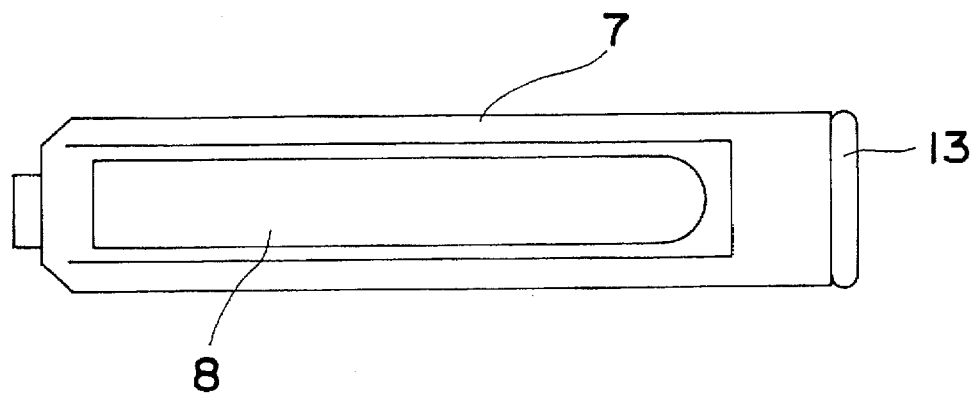
FIG. 12 is a plan view of the state where a syringe filled with pharmaceutical liquid is inserted into a radiation shielding device.
Figure 13:
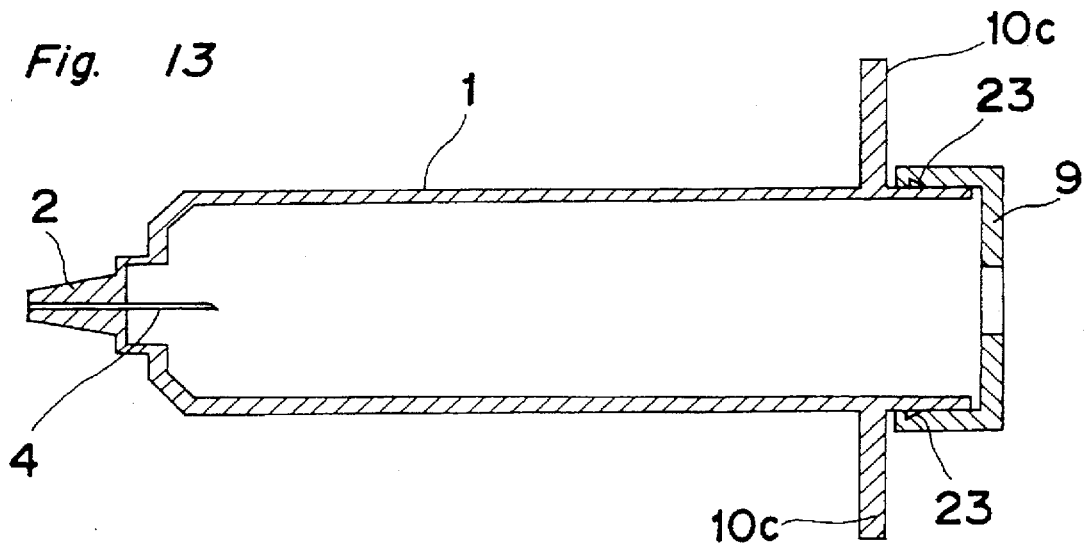
FIG. 13 is a sectional view of the syringe barrel sheath in FIG. 11 having a rear lid mounted thereto.
Figure 28:
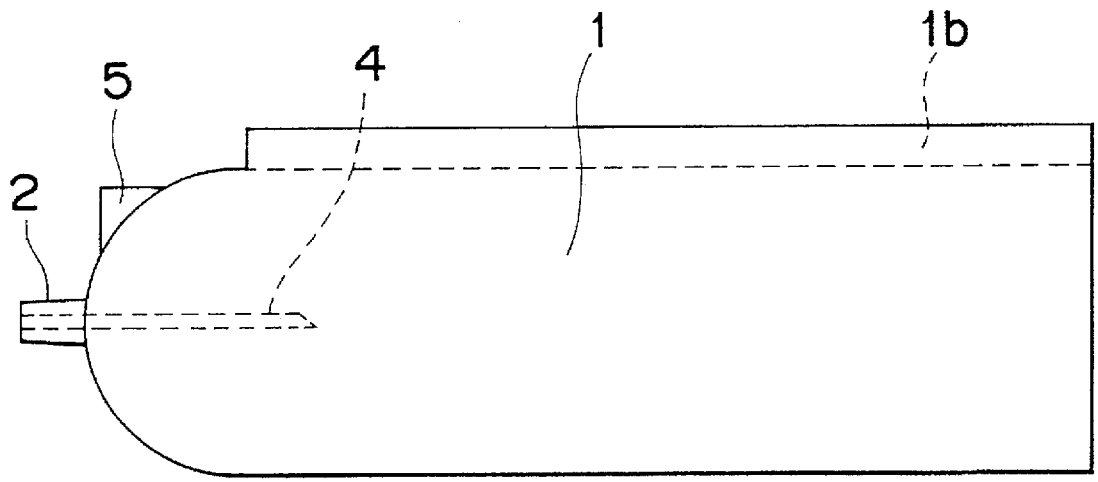
FIG. 28 is a side view of a syringe barrel sheath according to a further embodiment of the present invention.
Figure 29:
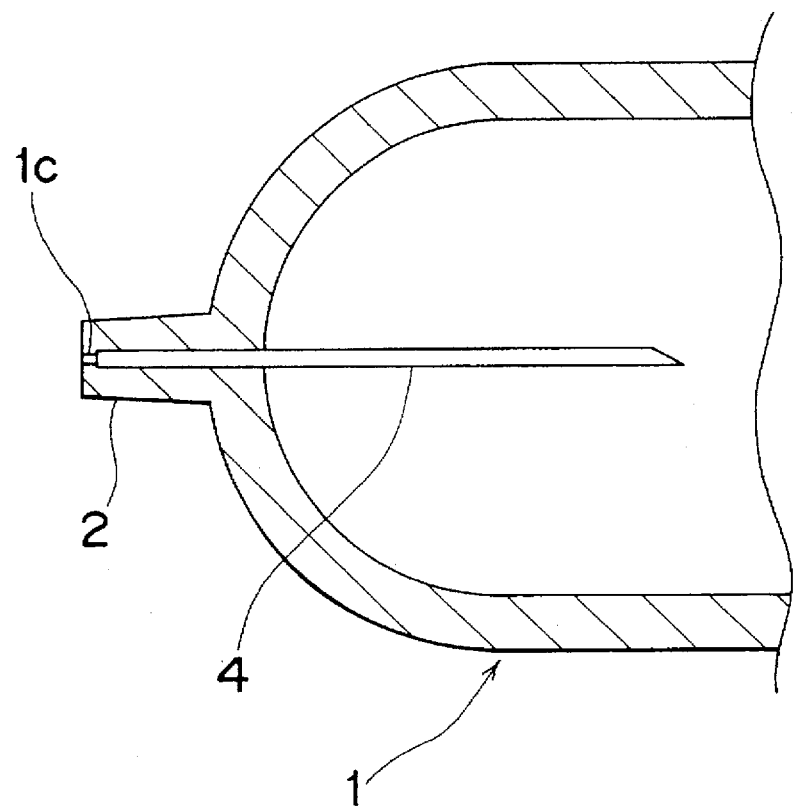
FIG. 29 is a partial sectional side view of a syringe barrel sheath according to a further embodiment of the present invention.

The main body 1 may be formed in such a configuration as to totally cover even the lead glass see-through window 8, other than in the above-described shape. In the case where the main body 1 covers the see-through window 8, a part of the main body 1 covering the see-through window 8 is, needless to say, made transparent. That is, instead of the cutaway 1a, the main body 2, 3 can have a transparent portion 1b for positioning a lead glass see-through window 8 of the radiation shielding device 7 thereat and covering it therewith to see the inside of the radiation shielding device 7 through the transparent portion 1b and the lead glass see-through window 8 thereof, as shown in FIG. 28. Although it does not matter whether the main body 1 is shorter than the above-discussed length, it is similarly safe to set a transfixing needle 4 which is not protected at the point thereof if the main body 1 is longer than the transfixing needle 4, and also the radiation shielding device 7 is inserted and fitted well in the main body 1 of the sheath. The main body 1 may also have flanges 10a to cover up the flanges 10b of the radiation shielding device 7 as shown in FIGS. 8–10. Alternatively, the flanges 10b of the radiation shielding device 7 can be eliminated, and instead flanges 10c may be provided only at the main body 1 of the sheath as illustrated in FIGS. 11–13. Further, as shown in FIGS. 11 and 13, there may be disposed, at the main body 1 and the flexible rear lid 9 of the radiation shielding device 7, a mechanism, e.g. engaging projections 23 or screws, for attaching/detaching the flexible rear lid 9 of the radiation shielding device 7.

Figure 14:
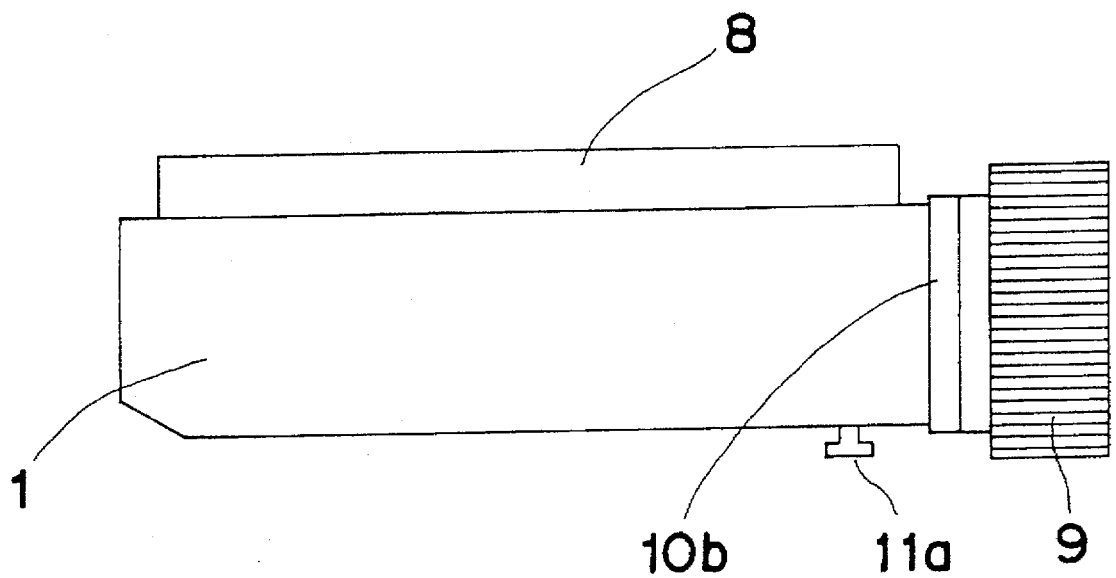
FIGS. 14 and 15 are a side view of the radiation shielding device equipped with a fixing mechanism and a plan view of a part of the device seen from below.
Figure 15:
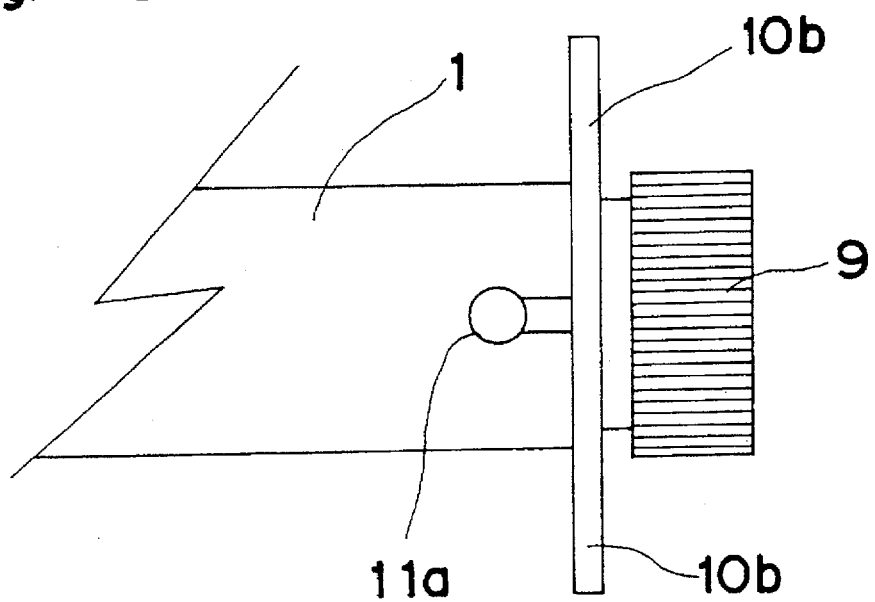
Figure 16:
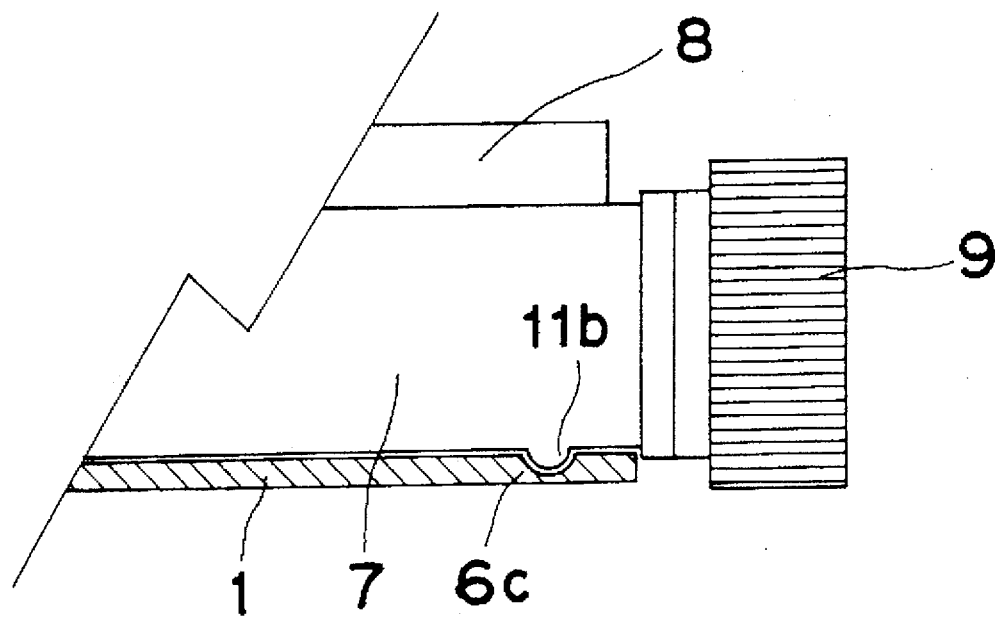
FIGS. 16 and 17 are sectional views of a rear part of a radiation shielding device equipped with another fixing mechanism and a part of a syringe barrel Sheath according to a further embodiment of the present invention.
Figure 17:
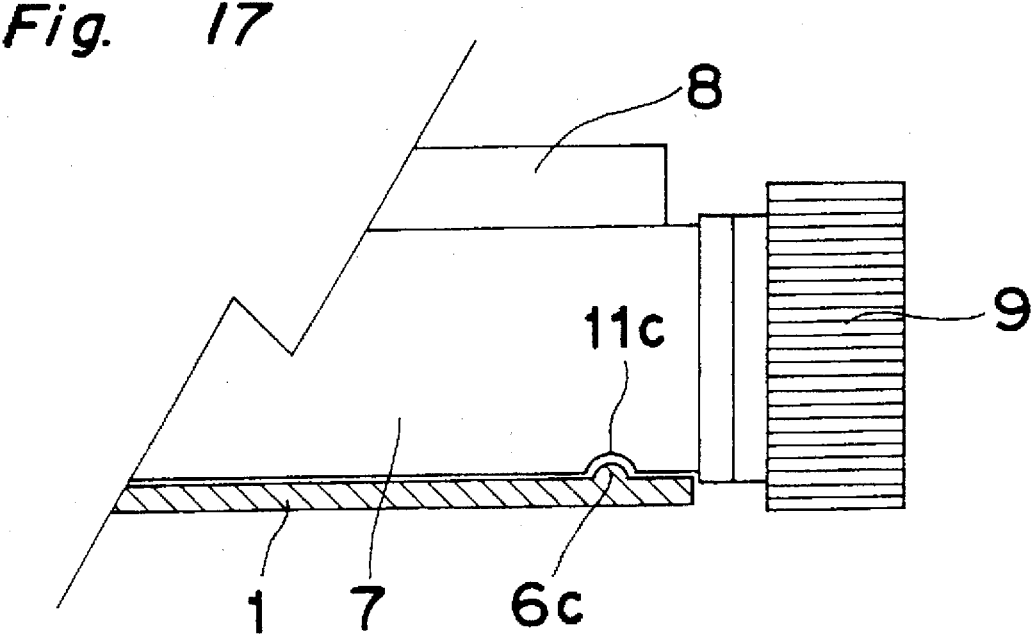
Figure 18:
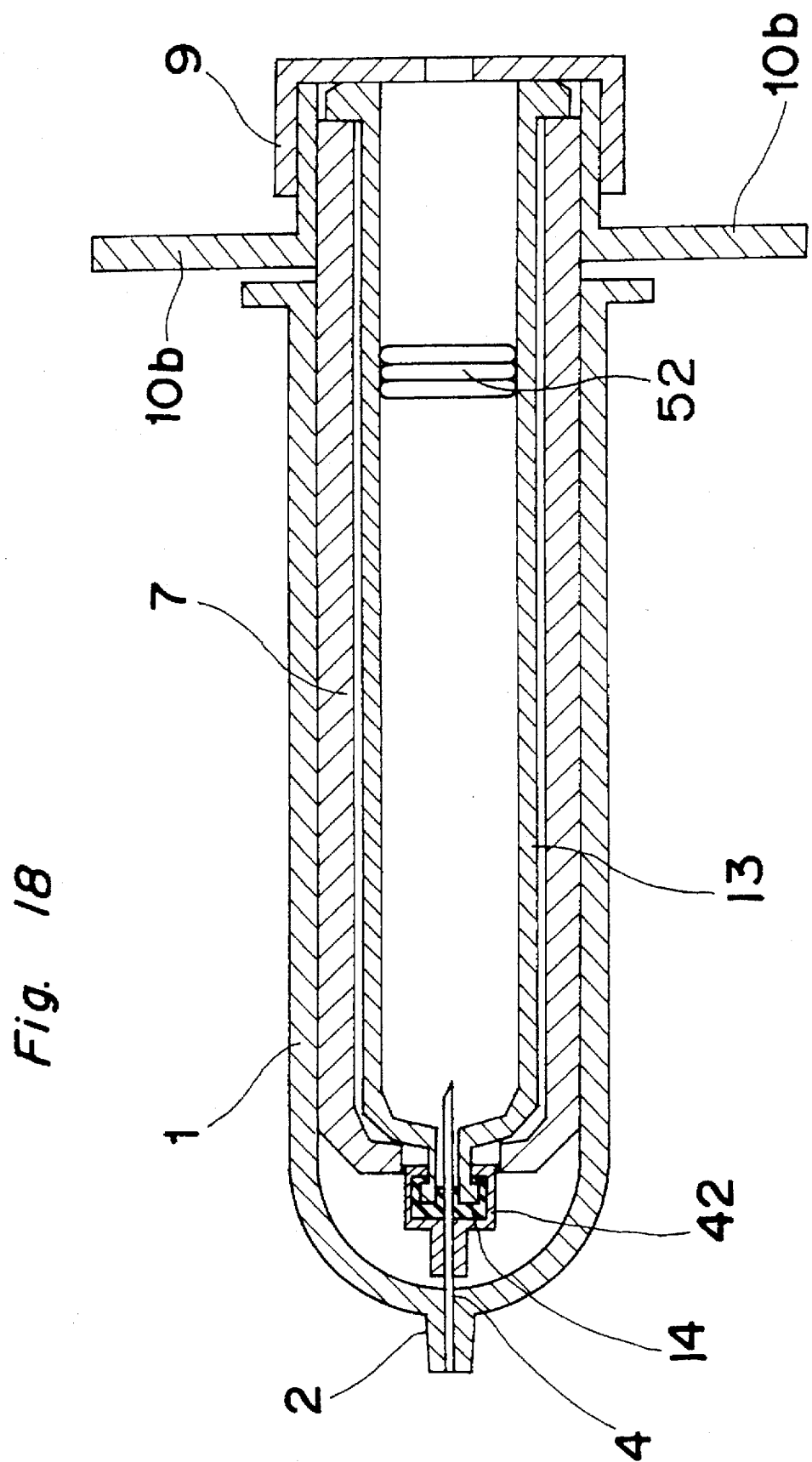
FIGS. 18, 19, and 20 are a sectional plan view, a plan view, and a side view of a syringe barrel sheath respectively according to a further embodiment of the present invention.
Figure 19:
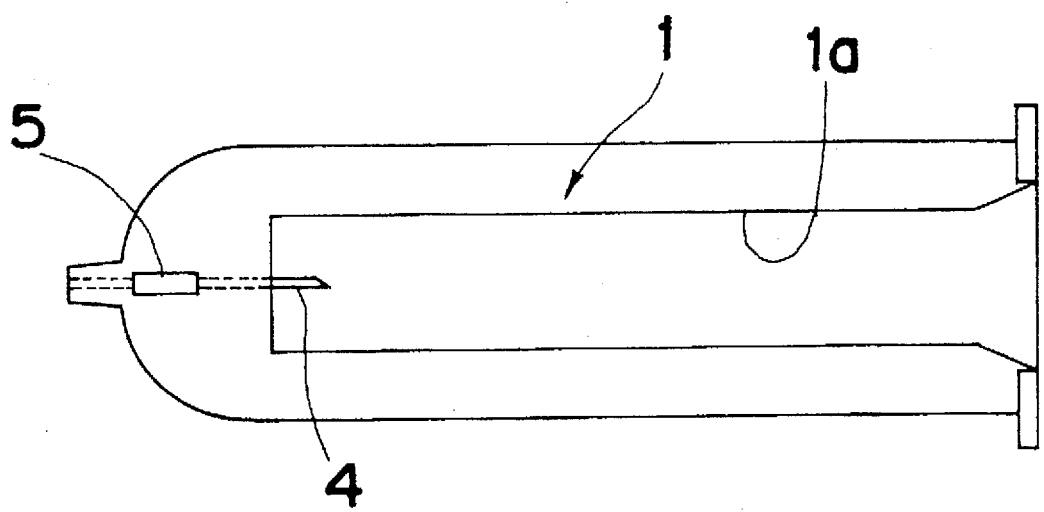
Figure 20:
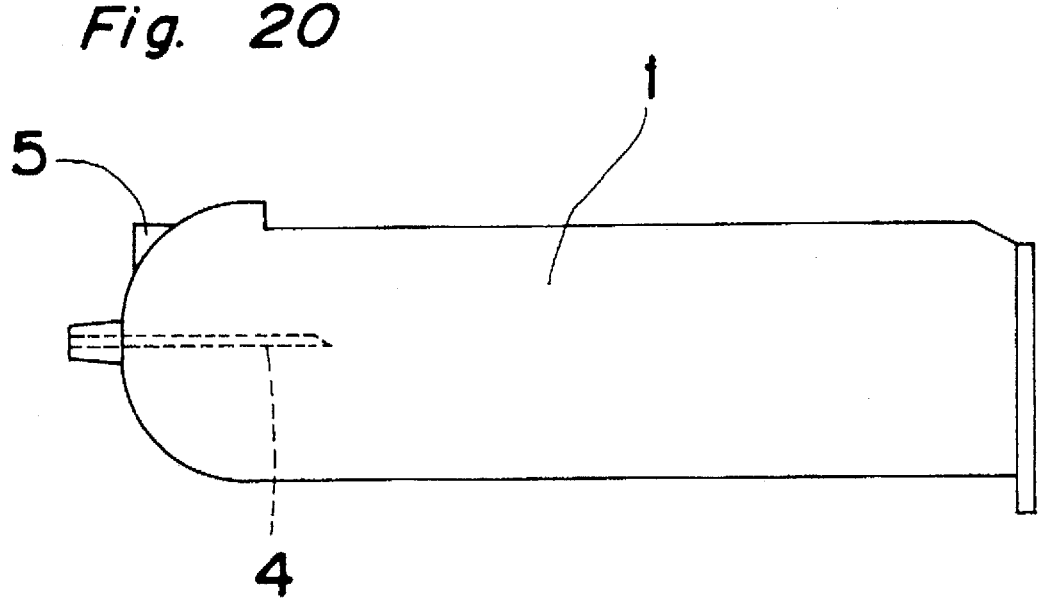
Figure 21:
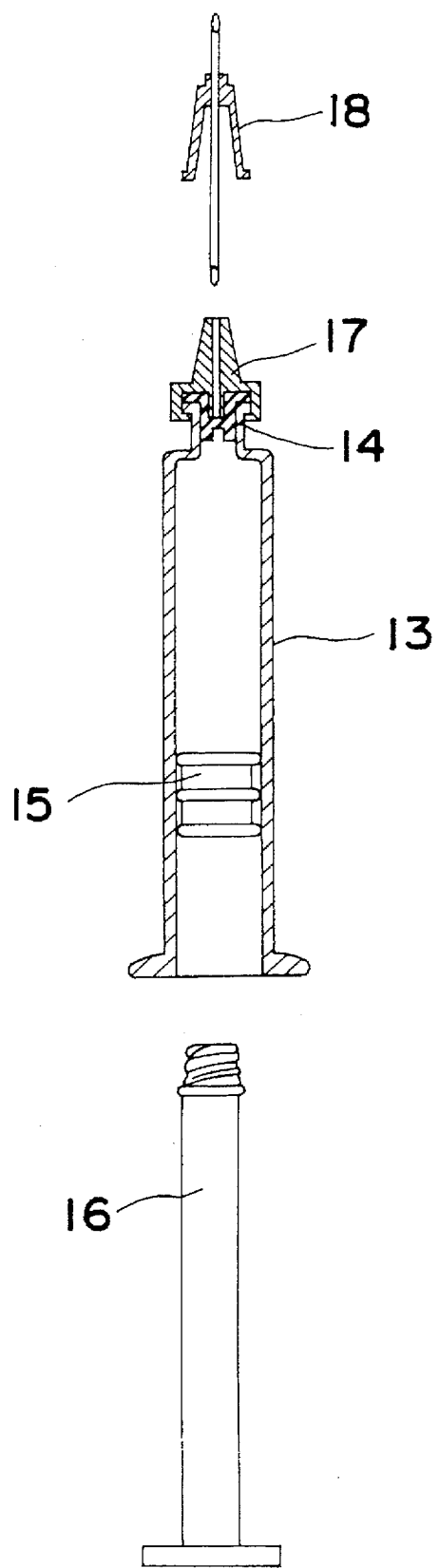
FIG. 21 is an exploded sectional view of a conventional syringe filled with pharmaceutical liquid before assembled into an operable state.
Figure 22:
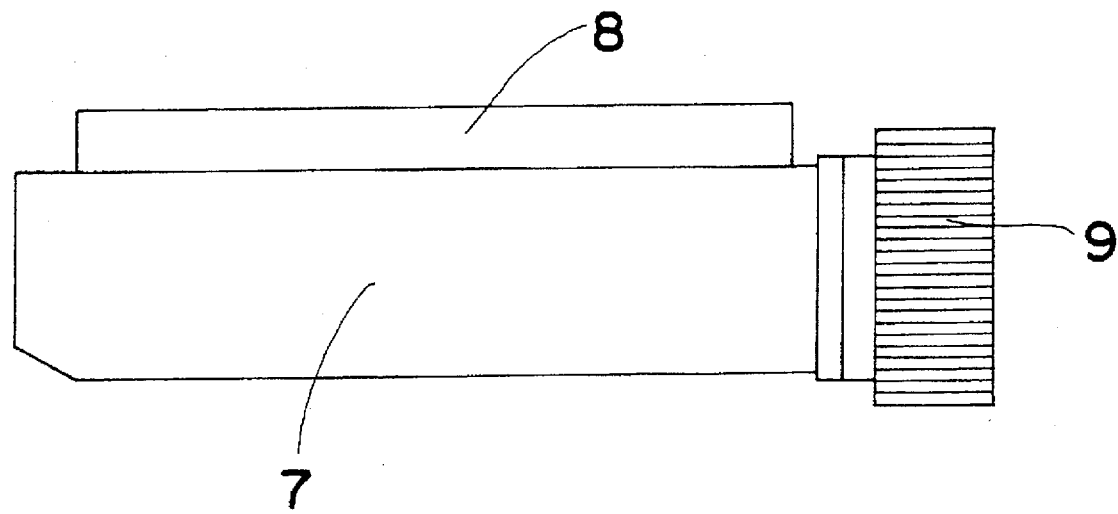
FIGS. 22 and 23 are a side view and a plan view of a conventional radiation shielding device.
Figure 23:
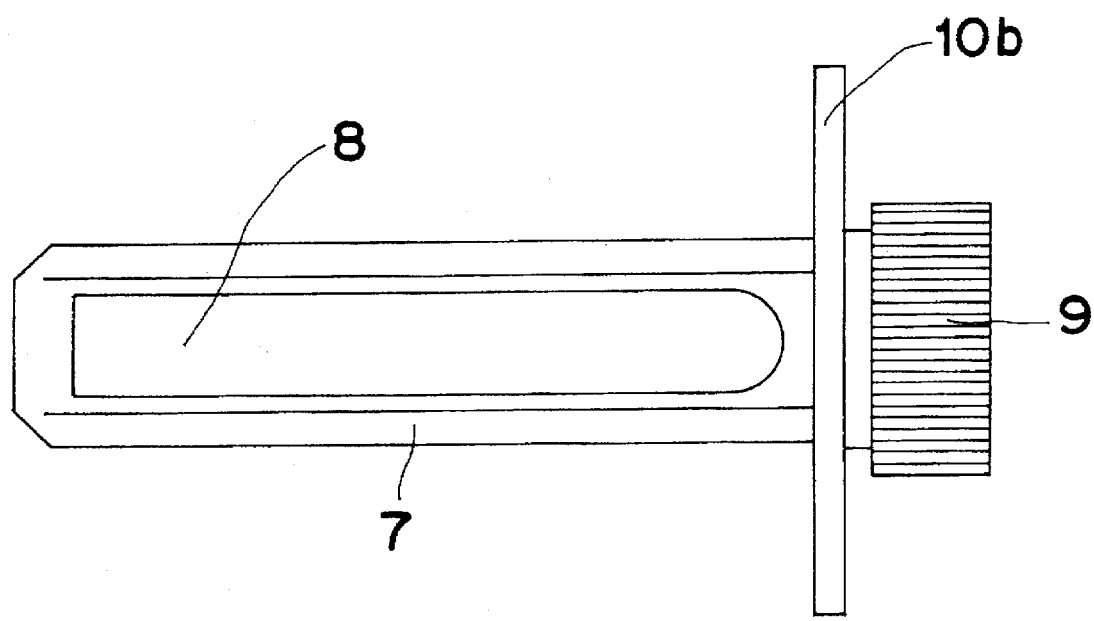
Figure 24:
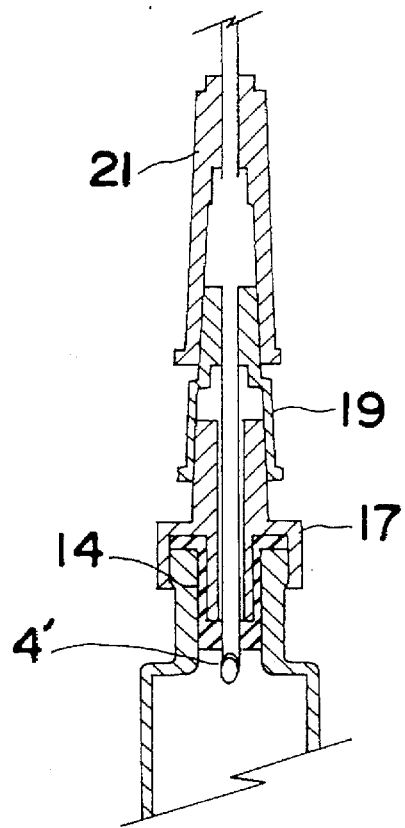
FIG. 24 is a sectional view of a conventional double luer needle.
Figure 25:
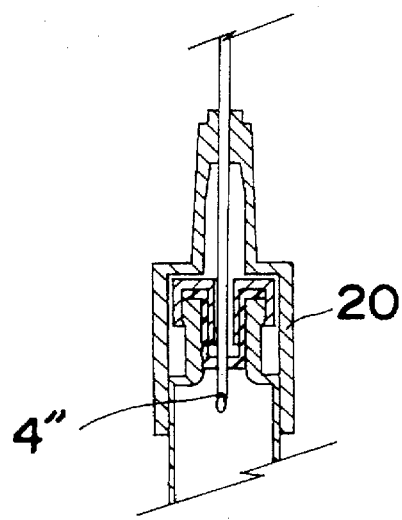
FIG. 25 is a sectional view of a conventional double-sided holder.

In order to fix the radiation shielding device 7 with the main body 1 of the sheath, the main body 1 is provided with the fixing notch 6a at a position corresponding to the projection 11a of the radiation shielding device 7 as in FIGS. 14 and 15. In a different arrangement in FIGS. 16 and 17, a projecting or recessed part 11b or 11c is formed at a part of the radiation shielding device 7, corresponding to which a recessed or projecting part 6b or 6c is positioned in the main body 1 to engage with each other. According to another arrangement as shown in FIGS. 8–10, hooks 12 are formed at the main body 1 to be fixedly meshed with corresponding flanges 10b of the radiation shielding device 7. The other fixing method than the above is employable so long as it is fully in conformity with the configuration of the radiation shielding device 7. For example, the inner configuration of a part or the whole of the sheath is formed in conformity with the outer configuration of the radiation shielding device 7 and made of flexible material, so that when the radiation shielding device 7 is fitted into the sheath, the device 7 closely contacts the sheath so that it is not easy to remove the device 7 from the sheath with the elastic force of the sheath applied to the device 7.

In a sheath according to another embodiment of the present invention, the inner diameter of a through hole 1c in the male luer 2 is smaller than the outer diameter of the transfixing needle 4 so as to certainly and easily connect the transfixing needle 4 into the through hole 1c of the sheath and prevent the transfixing needle 4 from protruding from the male luer 2 to the outside when the transfixing needle 4 penetrates the rubber plug 14 of the syringe.

Among various kinds of registering marks conceivable, it is appropriate to indicate a colored line registered at a portion of the main body 1 which corresponds to the center of the see-through window 8 of the radiation shielding device 7, or form a linear or rectangular cutaway or protuberance (e.g. as shown in FIG. 26) so as to enhance visibility.

In the construction of the present invention as described hereinabove, it becomes possible to select a diameter and a length of the disposable needle, which has a transparent part for connecting the male luer, fit for the purpose of dosage and confirm the blood vessel easily through a gap between a needle part of the disposable needle and the male luer in the transparent part of the disposable needle.

Moreover, the registering mark is effective to register the point of the disposable needle in the injecting direction before the disposable needle is mounted to the syringe. Accordingly, the operator, particularly, the fingers and hands of the operator are less exposed to radiation. The syringe is readily set for the injection of pharmaceutical liquid.

If the syringe filled with pharmaceutical liquid is already accommodated in the radiation shielding device before the radiation shielding device is used, the exposure to radiation is furthermore decreased.

Since the transfixing needle is present inside the main body of the sheath, the operator is secluded from danger to be inadvertently hurt by the transfixing needle when fitting the radiation shielding device or detaching the radiation shielding device from the main body of the sheath after use. Therefore, the operator is effectively protected.

Besides, if it is necessary to detach and dispose of the needle, it is settled by providing a detaching mechanism for the transfixing needle from the main body of the sheath.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A sheath and a radiation shielding device holding a syringe filled with pharmaceutical liquid, the syringe defining a front end, the sheath comprising:

a main body in which said radiation shielding device is fitted, said main body having a front end;

a male luer provided at the front end of said main body to which a disposable needle is mounted; and a transfixing needle mounted to said male luer and extending backward from said male luer into said main body to penetrate a rubber plug mounted at the front end of the syringe.

2. The sheath as claimed in claim 1, wherein the radiation shielding device defines a given outer configuration, and wherein said main body has an inner configuration in conformity with the outer configuration of the radiation shielding device.

3. The sheath as claimed in claim 1, wherein the radiation shielding device defines a given outer configuration, and wherein said main body has an inner configuration in conformity with the outer configuration of the radiation shielding device.

4. The sheath as claimed in claim 1, further comprising a mark situated on said main body for registering a disposable needle in an injection direction for the pharmaceutical liquid when the disposable needle is set on the male luer.

5. The sheath as claimed in claim 1, further comprising a mark situated on said main body for registering a disposable needle in an injection direction for the pharmaceutical liquid when the disposable needle is set on the male luer.

6. The sheath as claimed in claim 2, further comprising a mark situated on said main body for registering a disposable needle in an injection direction for the pharmaceutical liquid when the disposable needle is set on the male luer.

7. The sheath as claimed in claim 3, further comprising a mark situated on said main body for registering a disposable needle in an injection direction for the pharmaceutical liquid when the disposable needle is set on the male luer.

8. The sheath as claimed in claim 1, wherein said main body and said radiation shielding device each have fixing means for fixing said radiation shielding device with respect to said main body.

9. The sheath as claimed in claim 2, wherein the main body and a radiation shielding device include fixing means for fixing the radiation shielding device with the main body.

10. The sheath as claimed in claim 4, wherein the main body and a radiation shielding device include fixing means for fixing the radiation shielding device with the main body.

11. The sheath as claimed in claim 1, wherein the main body has a length longer than a length of the portion of the transfixing needle which extends from the inside of the male luer backward.

12. The sheath as claimed in claim 1, wherein the male luer has a through hole for fixing the transfixing needle therein, the hole having an inner diameter smaller than an outer diameter of the transfixing needle.

13. A sheath for a radiation shielding device holding a syringe filled with pharmaceutical liquid, the syringe defining a front end, the sheath comprising:

a main body in which the radiation shielding device is fitted, said main body having a front end;

a male luer provided at the front end of said main body to which a disposable needle is mounted;

a transfixing needle mounted to said male luer and extending backward from said male luer into said main body to penetrate a rubber plug mounted at the front end of the syringe; and a three-way cock as part of said male luer.

14. The sheath as claimed in claim 13, wherein said main body the radiation shielding device each have fixing means for fixing the radiation shielding device with respect to said main body.

15. A sheath for a radiation shielding device holding a syringe filled with pharmaceutical liquid, the syringe defining a front end, said sheath comprising:

a main body in which the radiation shielding device is fitted, said main body having a front end and a cutaway which is fitted for a lead glass see-through window of the radiation shielding device to be received in said main body;

a male luer provided at the front end of said main body to which a disposable needle is mounted; and a transfixing needle mounted to said male luer and extending backward from said male luer into said main body to penetrate a rubber plug mounted at the front end of the syringe.

16. A sheath for a radiation shielding device holding a syringe filled with pharmaceutical liquid, the syringe defining a front end, the radiation shielding device defining a given outer configuration, said sheath comprising:

a main body in which the radiation shielding device is fitted, said main body having a front end, an inner configuration in conformity with the outer configuration of the radiation shielding device, and a cutaway which is fitted for a lead glass see-through window of the radiation shielding device to be received in said main body;

a male luer provided at the front end of the main body to which a disposable needle is mounted; and a transfixing needlemounted to said male luer and extending backward from said male luer into said main body to penetrate a rubber plug mounted at the front end of the syringe.

17. A sheath for a radiation shielding device holding a syringe filled with pharmaceutical liquid, the syringe defining a front end, the sheath comprising:

a main body in which the radiation shielding device is fitted, said main body having a front end and a transparent portion for positioning a lead glass see-through window of the radiation shielding device thereat and fitted for the lead glass see-through window therewith to see the inside of the radiation shielding device through the transparent portion and the lead glass see-through window thereof;

a male luer provided at the front end of said main body to which a disposable needle is mounted; and a transfixing needle mounted to said male luer and extending backward from said male luer into said main body to penetrate a rubber plug mounted at the front end of the syringe.

\* \* \* \* \*